United States Patent

Levinson et al.

[11] 3,955,564
[45] *May 11, 1976

[54] METHOD OF IMPROVING OCULAR FIXATION, SEQUENTIAL SCANNING AND READING ACTIVITY IN DYSMETRIC DYSLEXIC CHILDREN

[76] Inventors: Harold N. Levinson, 15 Lake Road, Great Neck, N.Y. 11020; Jan Frank, 45 E. 42nd St., New York, N.Y. 10028

[ * ] Notice: The portion of the term of this patent subsequent to Oct. 22, 1991, has been disclaimed.

[22] Filed: Jan. 6, 1975

[21] Appl. No.: 538,967

Related U.S. Application Data

[63] Continuation-in-part of Ser. No. 516,796, Oct. 21, 1974, abandoned.

[52] U.S. Cl. ............................ 128/76.5; 128/2 R
[51] Int. Cl.² ...................................... A61H 5/00
[58] Field of Search .............. 128/76.5, 2 R, 2 N, 128/2 T, 2 Z

[56] References Cited
UNITED STATES PATENTS

| | | | |
|---|---|---|---|
| 2,795,993 | 6/1957 | Leverett et al. | 128/2 T |
| 3,000,271 | 9/1961 | Harvey et al. | 128/2.1 M |
| 3,030,944 | 4/1962 | Blau et al. | 128/2 N |
| 3,416,857 | 12/1968 | Lookabaugh | 128/2 T |
| 3,842,822 | 10/1974 | Levinson et al. | 128/2 R |

*Primary Examiner*—John D. Yasko
*Attorney, Agent, or Firm*—Bauer, Amer & King

[57] ABSTRACT

The use of an eye exercise to induce a mild and tolerable nystagmus in a dysmetric dyslexic child having a cerebellar-vestibular dysfunction, and in so doing call forth compensating mechanisms in the child which are effective in improving the child's ocular fixation, sequential scanning and reading activity.

The aforesaid calling forth of said compensating mechanisms beneficially provides a reflex reduction of the cerebellar-vestibular induced dysfunction of the dyslexic child. It is analogous to what occurs in amblyopia, in which compensation in the form of central functional suppression of vision in one eye is restored to in order to avoid double vision and the discomfort it gives rise to. Also, like amblyopia, if the dysfunctioning of the cerebellar-vestibular is not detected early and corrected, as by the compensation referred to, it might become irreversible in time.

In one preferred form the eye exercise is one which requires dysmetric dyslexic children to track sequential stimuli moving across their line of vision at a speed just below their blurring threshold. In another form, the dysmetric dyslexic children are required to identify selected static, fixation foreground objects and figures while the background, which has a distracting influence of a controllable degree, is moved at a speed at or below the "distraction" or blurring threshold.

5 Claims, 6 Drawing Figures

METHOD OF IMPROVING OCULAR FIXATION, SEQUENTIAL SCANNING AND READING ACTIVITY IN DYSMETRIC DYSLEXIC CHILDREN

This application is a continuation-in-part of application Ser. No. 516,796, filed Oct. 21, 1974 now abandoned.

The present invention relates to a method of improving the ocular fixation and sequential scanning skills of dysmetric dyslexic children, and more particularly to achieving this improvement by overcoming the dysfunction in ocular fixation and sequential scanning which exists in dysmetric dyslexic children.

As disclosed in U.S. Pat. No. 3,842,822, published on Oct. 22, 1974, our research has revealed that a cerebellar-vestibular dysfunction and sub-clinical nystagmus results in an impairment of ocular fixation and sequential scanning which in turn leads to dyslexia. This is contrary to the more widely accepted belief in the medical profession that the condition of organically determined dysmetric dyslexia is due solely or at least primarily to a dysfunction of the cortex.

We have also discovered that dysmetric dyslexic children sacrifice "seeing" a significant part of the moving visual field during tracking, in order to see a part of it clearly. That is, they fixate a third of the field clearly rather than blur the whole. This scomotization or field narrowing is a compensation against blurring.

As disclosed in the aforesaid U.S. Pat. No. 3,842,822, when reading material is moved at a selected speed across a display being viewed by both dysmetric dyslexic and normal children, the dysmetric dyslexic children will experience blurring at a significantly lower speed than the normal children. In this connection, we have demonstrated that young dysmetric dyslexic children blur at speeds one-quarter to one-half that of a normal child, this being in spite of the fact that, as just noted, dysmetric dyslexic children are able to fixate or "see" only one-quarter to one-half the field of normal children.

The discovery that dysmetric dyslexic children utilize a significantly restricted visual field, or in other words substantially scomotize their visual field, confirms that compensating mechanisms are being called upon to avoid the blurring which they experience and to maintain an optical fixation point. A further confirming example is the discovery that at or just before blurring, there is a reflex suppression of the nystagmus attempted or exerted by the child to enable himself to "see clearly." This is manifested, in part, by enlargement of the functional fixation zone in the child's eyes. The recognition of these compensating factors is an important aspect of the present invention. Specifically, the aforesaid is utilized to the extent that the within method, soon to be described, makes use of these compensating mechanisms, in that it intentionally produces this compensation by encouraging dysmetric dyslexic children to track sequential stimuli at speeds just below the blurring threshold. Operating at this level, the children do not experience anxiety, and yet there is stimulation, in the form of attempts to track sequential stimuli, which we have found results in the development of a nystagmus suppression or inhibition which, in turn, significantly facilitates tracking by dysmetric dyslexic children. We have also found that the stimulation produced by the within method results in an enlargement of the functional optical or retinal fixation zone, similar to the enlargement which occurs during diseases of the retina where a transfer of the retinal fixation zone takes place so that vision is spared.

Since dyslexia is typically defined as a reading disability, children suffering from dyslexia were not identified until they were discovered to be deficient readers. By using the screening procedures of the aforesaid U.S. Pat. No. 3,842,822, it is now possible to achieve an early identification of dyslexic children. This early identification, however, does not necessarily solve the problem. Indirectly, it may result in delaying the teaching of reading skills to a child known to be dysmetric dyslexic until he has reached a level of maturity to cope with the requirements of reading, and to this extent may spare the child emotional and psychological trauma. The young child however will have to wait until he reaches about ten to twelve years of age, depending upon his rate of maturation, since this is the age when the symptoms of the form of dyslexia discussed previously tend to lessen. The child is still in the unfortunate position of being as much as two years behind his age group, and may even be destined to remain a slow or non-reader for life because of possible irreversibility of the condition, as often occurs with amblyopia.

Broadly it is an object of the present invention to provide an effective method for accelerating the compensation process of a dysmetric dyslexic child, and to thereby correspondingly accelerate the time when such a child can participate, like normal children, in reading exercises, and to otherwise overcome the foregoing and other shortcomings of the prior art. Specifically, it is an object of the inventive method to make effective, at a time earlier than it would otherwise become effective, compensating mechanisms in dysmetric dyslexic children which overcome and thereby obviate the difficulties that these children have in performing reading activity.

The above brief description, as well as further objects, features and advantages of the present invention, will be more fully appreciated by reference to the following detailed description of the inventive method and of a presently preferred, but nonetheless illustrative, apparatus for practicing said method, said description to be read in conjunction with the accompanying drawings, wherein.

Reference is now made to the drawings wherein there is shown an appropriate projector apparatus, generally designated 10, for practicing the procedures or methods of the present invention. Apparatus 10, more particularly, is the one recommended for inducing a nystagmus or eye vibration of a selected extent in the dysmetric dyslexic child, the extent which is selected being that which is just below the "blurring" threshold of the child. That is, if this nystagmus is confined to this tolerable level, it will force a degree of concentration in the child which, in turn, will result in suppression of, and increased control over, the child's cerebellar-vestibular dysfunction, i.e., the impairment of the child's ocular fixation and sequential scanning abilities leading to dyslexia.

Figure 5:
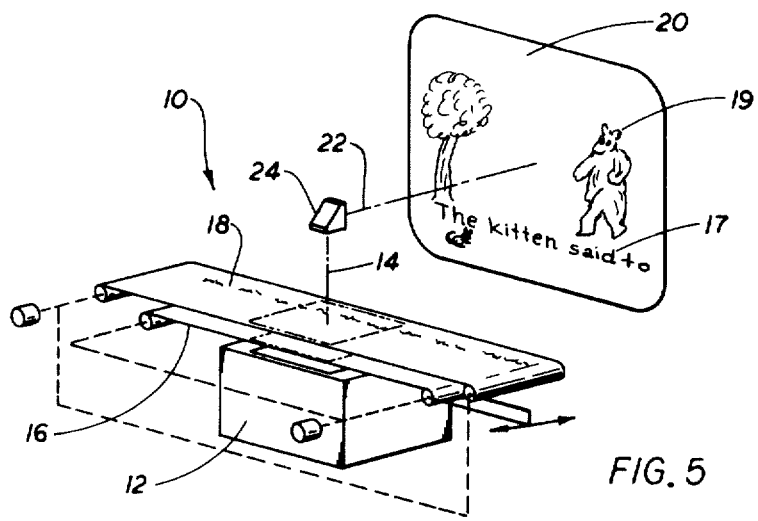
FIG. 5 diagramatically illustrates how said foreground and background are superimposed and used in the practice of the procedures and methods hereof.

As is perhaps best illustrated diagramatically in FIG. 5, apparatus 10 includes a light source 12 which is beamed, as along the path 14, through physically superimposed transparencies 16 and 18, functioning respectively as background 19 and foreground 17, so as to produce a composite visual display 20.

The beamed projection along the path 22 is achieved with a conventional projector or optical element 24 which may be a prism or the like. The projected visual display 20 thus consists, in part, of foreground which, in turn, may consist of symbols or the illustrated words "the kitten said to," designated 17, which foreground is on the transparency 18 and is projected by the overhead projector 24 to a viewing position as part of the composite visual display 20. The other part of the display 20 consists of background symbols or the like, as exemplified by the drawing of the bear, designated 19, which is set forth on the transparency 16 and similarly is projected by the overhead projector 24 into viewing position as part of the visual display 20.

Figure 4A:
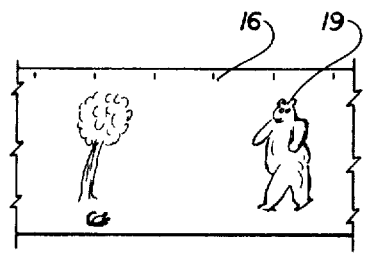
FIGS. 4a and 4b are related illustrations respectively showing the background and foreground of the visual display utilized in practicing the procedures and methods hereof.
Figure 4B:
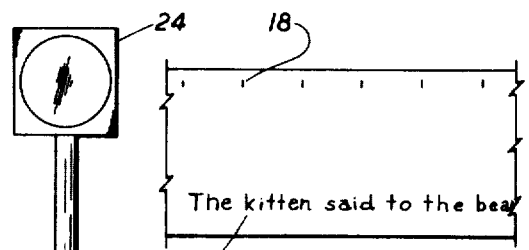

The portion of the transparency 16 containing the reproductions thereon which contribute to the projected background image 19 is set forth in FIG. 4a, while the coextensive portion of the transparency 18 containing the foreground text material 17 is set forth in FIG. 4b. As illustrated in FIG. 5, each transparency 16 and 18 is in the specific form of an elongated strip and, as will be described in greater detail subsequently, each is operatively arranged to be independently urged through movement at selected rates of speed. That is, the projected foreground 17 and background 19 can be moved at any selected speed, in feet per second, simultaneously, or the foreground material 17 can be held stationary while the background material 19 moved relative thereto, or vice versa.

Figure 1:
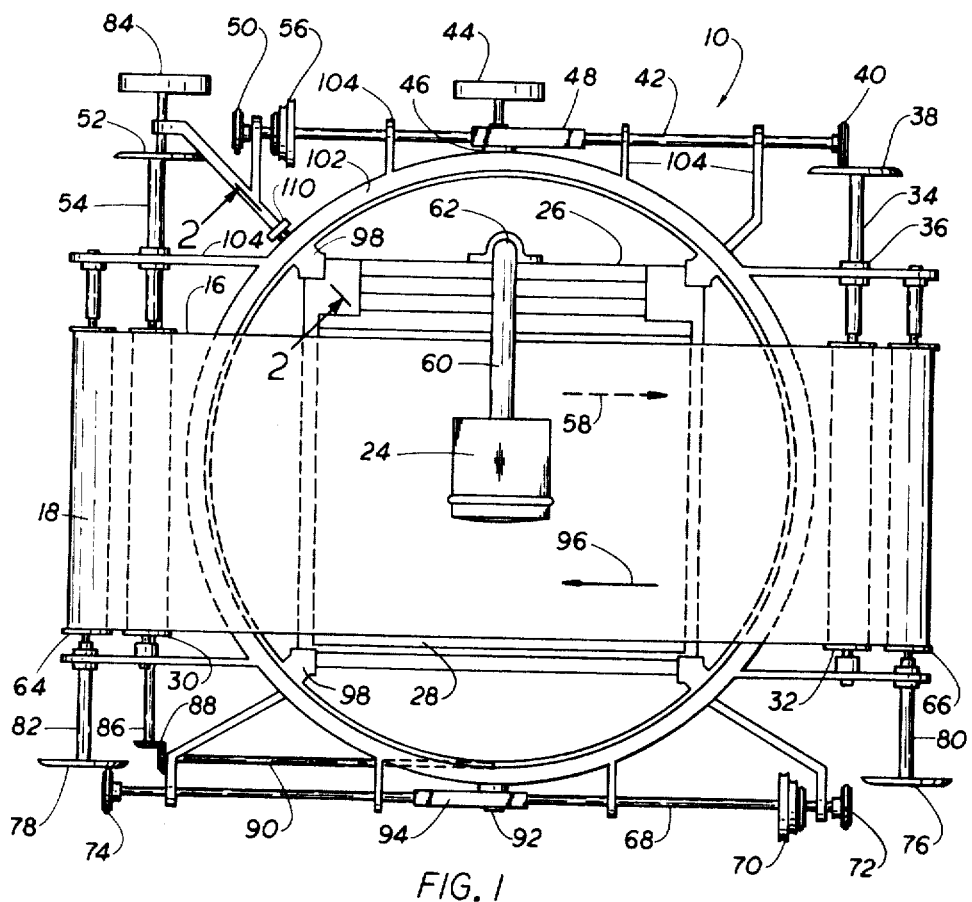
FIG. 1 is a plan view of an exemplary apparatus for practicing the compensation-inducing procedures or methods according to the present invention.
Figure 2:
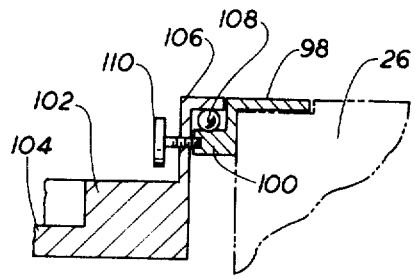
FIG. 2 is a partial side elevational view, in section taken on line 2—2 of FIG. 1, illustrating further structural features of said apparatus.
Figure 3:
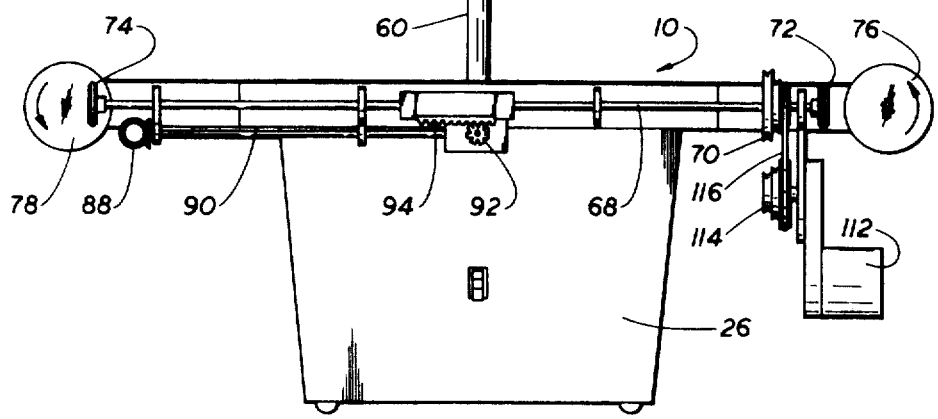
FIG. 3 is a side elevational view of the apparatus showing still further structural features.

As best illustrated in FIGS. 1–3, apparatus 10 includes a housing 26 for the light source 12 and has a transparent panel 28 as its upper surface. The background transparency strip 16 is arranged to be urged through movement across panel 28, being entrained on feed roller 30 at one end and on take-up roller 32 at its opposite end. To power take-up roller 32 in rotation, there is provided a spindle extension 34 on this roller, appropriately mounted in bearings, as at 36, and terminating in a driven friction disc 38. As illustrated in FIG. 1, in driving relation with disc 38 is driving disc 40 mounted on rod 42 which is shiftable in position by turning manipulation of the control knob 44 of pinion 46 in meshing engagement with rack 48. The counterpart of driving disc 40 is disc 50 mounted at the opposite end of rod 42 and shiftable into driving relation with the friction surface of driven disc 52 on the spindle extension 54 of the supply roller 30. To power the rod or drive shaft 42 in rotation, there is a step pulley 56 having a pulley drive connection to an electric motor or the like. It should be readily appreciated that not only do the driving discs 40 and 50 selectively drive the rollers 32 and 30 in rotation, but by properly locating the disc 40 relative to the rotation axis of the roller 32, control can be exercised over the speed at which roller 32 rotates, and thus the speed at which the transparency strip 16 is advanced along the path 58 beneath the overhead projector 24.

In the above regard, projector 24 is arranged in proper projecting relation to the transparency 16 and also to the transparency strip 18, by being mounted on the end of an L-shaped cylindrical rod 60. Proper positioning of the projecting element 24 is achieved by pivotally mounting rod 60, as at 62, on the housing 26.

In a very similar fashion as that already described, transparency strip 18 is also operatively arranged for movement at selected speeds in projecting relation to the overhead projecting element 24. Specifically, and as illustrated, a supply length of the transparency strip 18 is supported on the supply roller 64 and is advanced therefrom, beneath the projecting element 24, and attached to the take-up roller 66. A laterally shiftable rod or drive shaft 68 is provided having a step pulley construction 70 in driving relation via pulley belt 116 and pulley 114 with an electric motor 112 (FIG. 3). Said shaft 68 has mounted at opposite ends drive discs 72 and 74. These discs are selectively moved into driving relation with driven discs 76 and 78 on extensions 80 and 82 of the take-up roller 66 and supply roller 64, respectively. Since it is convenient to have the control for the rollers 64 and 66 on the same side as control 44, the control knob 84 thereof is located adjacent the knob 44 and has extended therefrom a rod 86 in meshing engagement, as at 88, with a further control rod 90. Rotation of rod 90 in turn causes, as best illustrated in FIG. 3, rotation in pinion 92 which is in meshing engagement with rack 94. Thus the direction of the shifting or control movement in the drive shaft 68 selects which of the driven discs 76 or 78 is to be powered in rotation. As illustrated in FIG. 1, the driving connection is made between discs 74 and 78 which produces directional movement 96 in the transparency strip 18 returning the same to the supply roller 64.

To provide additional flexibility either in the manner or in the orientation in which the component parts of the visual display are set forth in the projection being viewed by the examination group, the overhead projection 24 and the structure mounting and controlling the transparency strips 16 and 18 are rotatably mounted relative to the light source housing 26. In this respect, as illustrated in FIG. 2, mounted about the periphery of the housing 26 is a ring 98 having a lower laterally extending track 100. An outer ring-like body is mounted for rotative movement about the housing 26. Body 102 has rods connecting it to all of the previously described structures for supporting and controlling the transparency strips 16 and 18, said connecting rods being individually and collectively designated 104. The other end of body 102 has a construction providing an upper track 106. Between the tracks 100 and 106 are circumferentially spaced ball bearings 108 which enable rotational traverses in the body 102 relative to the stationary housing 26. A threadable member 110 is provided to maintain any selected rotated position of ring 102 relative to the central housing 26.

The foregoing apparatus 10 is merely exemplary of a device for producing a visual display 20 that is useful in inducing or requiring reading activity in a group or individual dyslexic child situated in viewing position before the display 20. Specifically, this reading activity consists of such child being required to read or recognize the display materials 17, 19 while these materials are being moved at a selected rate of speed from left to right, as viewed in FIG. 5. Experimentation with the apparatus 10 has indicated that imposing this requirement on the child results in his experiencing an eye vibration, or back-and-forth eye movement, at a frequency or number of beats per second which is related to the feet-per-second speed of the moving visual display 20. This eye movement, measured as a number of beats per second, can be carried beyond the child's tolerance threshold, which will be understood to be the point when the child experiences blurred or scrambled vision. In this connection, it is generally understood that in order to see something clearly, the eyes must fix on the object. When there is eye movement, however, or movement interfering with this visual fixation, the result is blurred or scrambled vision.

Children with normal functioning cerebellar-vestibular circuits can tolerate a certain extent of eye vibration or beats per second without complaining of blurred vision. This is what is referred to herein as the normal threshold level, i.e., the level of eye movements or beats per second at which there is clear vision, but beyond which there is blurred vision, for said referred to normal children. However, for dysmetric dyslexic children, the tolerance for eye vibrations or beats per second is much less, since such children start off with a sub-clinical eye vibration or nystagmus and dysmetric ocular pursuit.

Using the apparatus 10 described herein, experiments with children of various ages have produced significant data on the blurring or scrambling speeds of normal children compared to dysmetric dyslexic children. The experiments utilized words set forth on the transparency strip 18 that had 1-½ inch capital letters, ¾ inch lower case letters, and spacings of ¾ inch between letters and 4 inches between words, projected as said texual material 17 approximately 6 feet into display position. The younger dysmetric dyslexic children experienced blurred or scrambled visualization of the material 17 at half the running speed in the display 20 that could be tolerated by normal children of the same age. Highlights of the experiment are set forth in the below table.

| | Speeds at which blurring or scrambling occurs | |
|---|---|---|
| | Moving foreground 17 Fixed background 19 | Fixed foreground 17 Moving background 19 |
| Normal children of ages 4 to 8 years | 6 to 9 feet/sec | No blurring of foreground 17 |
| Dysmetric dyslexic children of ages 5 to 8½ years | 2.2 to 5 feet/sec | Blurring of foreground 17 at background speeds of 4 feet/sec |

Another effective nystagmus inducing method, which according to the present invention in turn induces compensation in the dyslexic child, which is practiced using the apparatus 10 consists of the following. The child is required to have visual fixation on a selected portion of the foreground material 16, such as the word "kitten." When the child indicates that this has been done, for example, by an appropriate hand signal, the background material 19 is then placed in motion. The moving background material 19 interferes with the ability to maintain visual fixation on the foreground image 17. That is, since the dysmetric dyslexic child has the aforesaid sub-clinical nystagmus, this has the unfortunate result of moving his eye focus from the target 17 to an adjacent area, which consists of the moving background or symbols 19. Here again, the object is to move the background 19 at just that speed where the dyslexic child is able to maintain his ocular fixation on the target 17 and then have the child identify changing foreground objects 17. This aids the child in developing background suppression ability, and in improving his fixation ability.

To summarize, we have found that through concentration called forth by repetition of the eye exercises represented by the aforesaid foreground and background display movements, that compensating mechanisms overcoming the impairments of a dysmetric dyslexic child, which usually are only available after a longer period of maturation and compensation, are much sooner effective to assist the child in suppressing his nystagmus and enlarging his functional optical fixation zone. The result is significantly improved targeting and fixation performance on the part of the child during reading activity. This is demonstrated in higher speeds before blurring occurs.

A latitude of modification, change and substitution is intended in the foregoing disclosure, and in some instances some features of the methods herein described can be employed without a corresponding use of other features. Accordingly, it is appropriate that the appended claims be construed broadly and in a manner consistent with the spirit and scope of the invention herein.

What is claimed is:

1. An eye exercise procedure for improving ocular fixation, sequential scanning and reading performance in a child previously identified as having a cerebellar-vestibular dysfunction resulting in dyslexia, said procedure comprising the step of inducing an eye oscillation of a selected extent which is normally below the threshold level producing blurred vision for said child, whereby repetition of said induced eye oscillation results in compensation for the child's cerebellar-vestibular induced dysfunction.

2. The eye exercise procedure as defined in claim 1 wherein said eye oscillation which is induced in said child is that resulting from a visual display moving across the line of vision of said child at a selected rate of speed.

3. The eye exercise procedure as defined in claim 2 wherein for a dysmetric dyslexic child in an age group under 9 years, said rate of speed is slightly less than 5 feet per second.

4. An eye exercise procedure for inducing compensation of a cerebellar-vestibular dysfunction producing dyslexia in a child, said procedure comprising the steps of requiring the visual fixation of said child upon a point on the foreground of a visual display having a movable background, moving said background at a speed selected to induce a mild nystagmus interfering with said visual fixation and which is below the threshold level producing blurred vision in said child, and having the child identify changing foreground fixation objects against said moving background.

5. The eye exercise procedure as defined in claim 4 wherein said foreground material consists of words and said background material consists of pictorial representations, and said background material is moved at a rate of speed of slightly less than 4 feet per second.

* * * * *